United States Patent [19]

Koike et al.

[11] 4,076,721
[45] Feb. 28, 1978

[54] PROCESS FOR PRODUCING SACCHARIN

[75] Inventors: Wataro Koike; Takahiro Kimoto, both of Shizuoka; Sadayoshi Matsui, Shimizu, all of Japan

[73] Assignee: Ihara Chemical Industry Co., Ltd., Tokyo, Japan

[21] Appl. No.: 677,255

[22] Filed: Apr. 15, 1976

[30] Foreign Application Priority Data

Feb. 7, 1976 Japan ............................ 51-12461
Jun. 11, 1975 Japan ............................ 50-70311

[51] Int. Cl.$^2$ ............................ C07D 275/06
[52] U.S. Cl. ............................ 260/301; 560/18; 560/14
[58] Field of Search ............................ 260/301

[56] References Cited

U.S. PATENT DOCUMENTS 2,667,503  1/1954  Senn ............................ 260/301

Primary Examiner—R. Gallagher
Attorney, Agent, or Firm—Oblon, Fisher, Spivak, McClelland & Maier

[57] ABSTRACT

An o-sulfobenzimide having the formula:

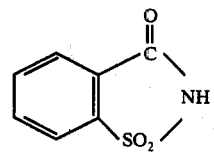

is prepared by reacting phosgene with a methylbenzoate-o-sulfonate having the formula:

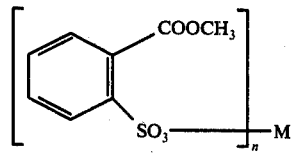

(I)

wherein M represents potassium or calcium, $n$ is 1 when M is K and $n$ is 2 when M is Ca, in an inert organic solvent in the presence of dimethylformamide; and then reacting ammonia with the reaction product.

11 Claims, No Drawings

PROCESS FOR PRODUCING SACCHARIN

BACKGROUND OF THE INVENTION

1. Field of the Invention

The present invention relates to a process for producing o-sulfobenzimide (1.2-benzoisothiazole-3-on-1.1-dioxide) which is useful as a medicinal agent (sweetener for diabetics), as food additives (sweetener) and as intermediates for agricultural chemicals in high yield by using a methylbenzoate-o-sulfonate which is easily obtained from o-chlorobenzoic acid by unique reaction steps.

2. Description of the Prior Art

In the past, 1.2-benzoisothiazole-3-on-1.1-dioxide having the formula:

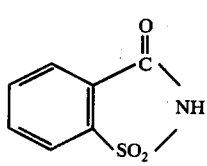

has been produced by the following sequence of reaction steps shown in Reaction scheme (I) in which: (1) toluene is chlorosulfonated; (2) o-toluenesulfochloride and p-toluenesulfochloride produced in the first step are separated and purified; (3) o-toluenesulfochloride separated and purified in the second step is reacted with ammonia; and (4) o-toluenesulfonamide produced in the third step is oxidized with a solution of bichromate in conc sulfuric acid. (J. Am. Chem. Soc., 1, page 426, 1879; BP No. 174,913 and BP No. 682,800)

Reaction scheme (1):

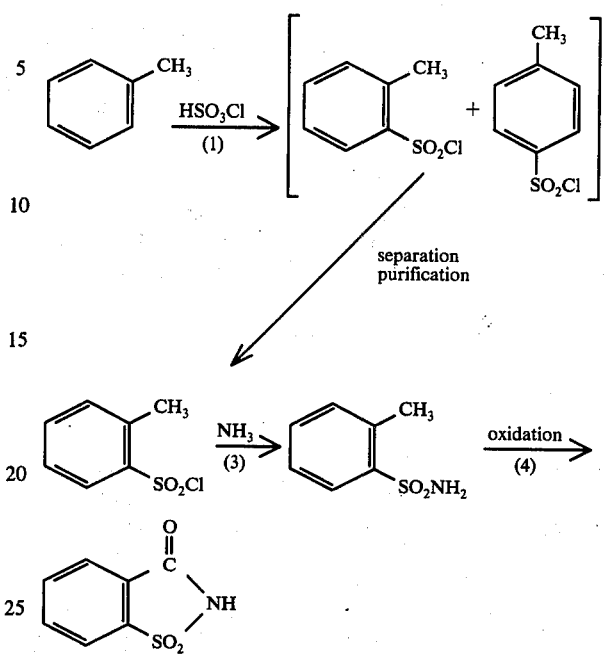

1.2-Benzoisothiazole-3-on-1.1-dioxide has also been produced by the reaction sequence shown in Reaction scheme (2), in which: (1) phthalic anhydride is reacted with ammonia; (2) phthalimide produced in the first step is subjected to the Hoffmann reaction; (3) o-aminobenzoic acid produced in the second step is diazotized; (4) sodium sulfide is reacted with the diazobenzoic acid produced in the third step; (5) sodium dithiodibenzoate produced in the fourth step is treated with an acid; (6) dithiodibenzoic acid produced in the fifth step is methyl esterified; (7) dimethyl dithiodibenzoate produced in the sixth step is reacted with chlorine; and (8) methyl o-sulfochlorobenzoate produced in the seventh step is reacted with ammonia. (Chemical Engineering, Vol. 61, No. 7, page 128, 1954).

Reaction scheme (2):

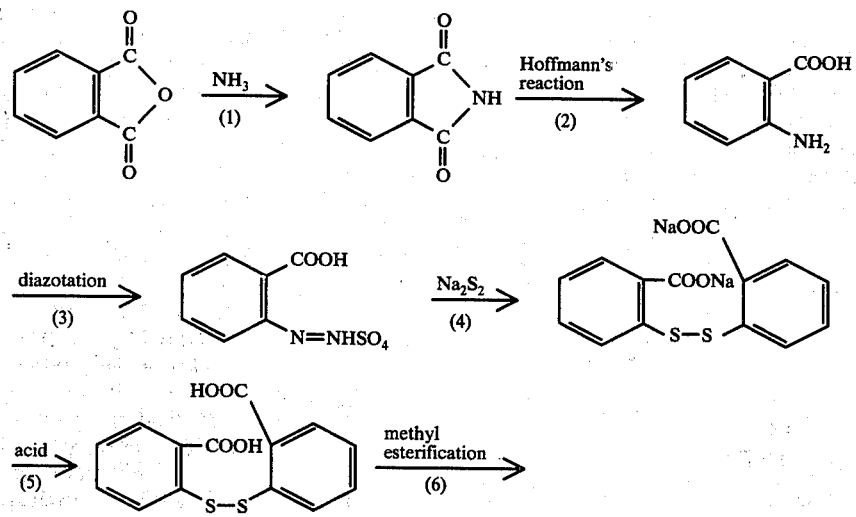

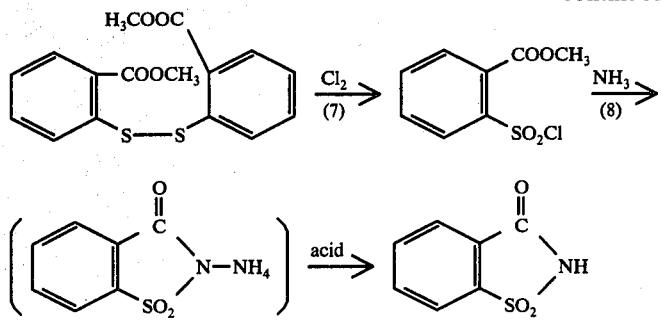

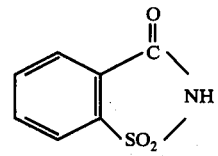

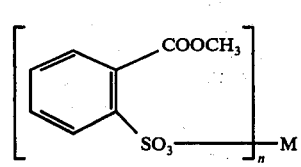

In the conventional process of Reaction scheme (1) large amounts of p-toluene-sulfochloride are produced from toluene as by-product together with o-toluenesulfochloride in the first step. Accordingly, the separation and purification procedures of the second step are quite troublesome. That is, the reaction mixture formed in the first step is poured into water to precipitate crystals of p-toluenesulfochloride and the crystals are centrifugally separated. The oily product of o-toluenesulfochloride which remains is further cooled to precipitate crystals of p-toluenesulfochloride, and the operation is repeated. However, it is difficult to separate all of the p-toluenesulfochloride from the oily o-toluenesulfochloride. Because of these difficulties, it is necessary to separate p-toluenesulfonamide as a by-product after the reaction with ammonia in the third step. In the fourth step of the reaction sequences it is necessary to treat a large amount of the waste acid from the bichromate and conc. sulfuric acid oxidation solution used in the fourth step. The process is also complicated by the necessity of using a large electrolyzer in the recovery and reuse of the chromium oxide formed as the reduced product from the bichromate oxidant. Moreover, a serious disadvantage of the conventional process is the fact that both o-toluenesulfonamide and p-toluenesulfonamide are believed to cause cancer. Because these materials are produced in the conventional process, it is necessary to separate the toxic compounds to purify the product. If the toxic compounds remain with 1.2-benzoisothiazole-3-on-1.1-dioxide in the use of the same as a food additive, there is the possibility of adverse affects on the human body. Accordingly, the conventional process is not a hygienically safe process.

In the conventional process of Reaction scheme (2) phthalic anhydride is used as the starting material, and it is necessary to use an eight step reaction sequence. Accordingly, the operation is complicated and it is difficult to attain high yields of 1.2-benzoisothiazole-3-on-1.1-dioxide such as about 50% based on the phthalic anhydride starting material. These processes are not satisfactory as industrial methods.

SUMMARY OF THE INVENTION

Accordingly, one object of the present invention is to provide a process for producing o-sulfobenzimide having high purity in high yield.

This object and other objects of the invention have been attained by providing a process for producing o-sulfobenzimide having the formula:

by reacting phosgene with a methylbenzoate-o-sulfonate having the formula:

$$\left[\begin{array}{c}\includegraphics\end{array}\right. \left.\begin{array}{c}COOCH_3 \\ SO_3{-}\end{array}\right]_n M \quad (I)$$

wherein M represents potassium or calcium; n is 1 when M is K and n is 2 when M is Ca, an inert organic solvent in the presence of dimethylformamide, and then reacting ammonia with the reaction product.

DETAILED DESCRIPTION OF THE PREFERRED EMBODIMENTS

Various processes have been studied for producing o-sulfobenzimide from the methylbenzoate-o-sulfonate, because the methylbenzoate-o-sulfonate can be easily produced in high efficiency from o-chlorobenzoic acid. As a result, it has been found that methyl o-chlorosulfonylbenzoate can be easily produced by reacting phosgene with the methylbenzoate-o-sulfonate in the presence of dimethylformamide, and the desired o-sulfobenzimide compound having high purity can be easily produced in high yield by reacting ammonia with methyl-o-chlorosulfonylbenzoate.

Heretofore, phosphorus pentachloride, phosphorus oxychloride, and the like have been used as chlorinating agents for alkali metal salts of aromatic sulfonic acids. (Organic Synthesis, collective Vol. I, Page 84, 1941). However, these chlorinating agents are expensive and in the reactions, phosphorus oxychloride or metaphosphoric acid, or the like are produced as by-products. Accordingly, it has been necessary to distill and purify the product after the reaction. However, the products obtained by this procedure are highly colored and the yields of the product are small. Because of these difficulties with the conventional processes using these chlorinating agents, it is difficult to produce o-sulfobenzimide of high purity in high yield from the methylbenzoate-o-sulfonate obtained by the conventional process in comparison to the present technique which uses chlorinating agents in the presence of dimethylformamide.

The process of the invention can be shown by the following Reaction scheme (3).

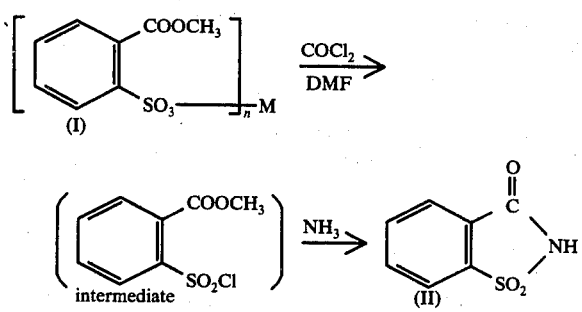

M and $n$ in the equation are as defined above and DMF represents dimethylformamide.

The methylbenzoate-o-sulfonate (I) used as a starting material in the process of the invention can be easily produced in yields greater than 80% from o-chlorobenzoic acid as shown by Reaction schemes (4)-(i) and (4)-(ii), by reacting o-chlorobenzoic acid with sodium sulfite in an aqueous solution of sodium hydroxide in the presence of a catalytic amount of cupric sulfate with stirring at 160°–200° C, adjusting the pH of the reaction mixture to 2–4 with conc. hydrochloric acid, and then precipitating a metal salt of o-sulfobenzoic acid by adding potassium chloride or calcium chloride to the acidic solution. In the second technique a metal salt of o-sulfobenzoic acid is reacted with methanol in the presence of a catalytic amount of sulfuric acid or hydrogen chloride at 80°–120° C.

ene, xylene, chlorobenzene, dichlorobenzene and the like.

The amount of dimethylformamide used as the catalyst in the first step is in a range of 0.01–0.3 mole, preferably 0.03–0.1 mole per mole of the methylbenzoate-o-sulfonic acid group ($CH_3OOC$-Ph-$SO_3$) in compound (I). If the amount of dimethylformamide employed is less than 0.01 mole, the reaction rate is slow thus resulting in long reaction times. If the amount is more than 0.3 mole, the reaction rate is high, but a resinous material is produced as a by-product which results in a colored o-sulfobenzimide product (II). The resinous material decreases the purity and yield of the product. It is also not preferable to use a large amount of dimethylformamide from the economic viewpoint.

In the reaction of phosgene with a metal methylbenzoate-o-sulfonate compound in the first step of the reaction sequence, phosgene can be directly introduced into an inert organic solvent solution of the methylbenzoate-o-sulfonate (I) in the presence of dimethylformamide with stirring, or it can be introduced by adding a solution of phosgene in an inert organic solvent such as carbon tetrachloride, toluene, or the like to the solution. The amount of phosgene employed is usually in a range of 1.0–1.2 mole per mole of methylbenzoate-o-sulfonic acid group in compound (I). The reaction of the first step is conducted at 10°–80° C, preferably 20°–50° C. If the reaction is conducted at relatively low temperature, the reaction rate is slow thus resulting in long reaction times. If the reaction is conducted at a temperature greater than 80° C, the reaction rate is high, but a resinous material is produced as by-product thus producing Reaction scheme (4):

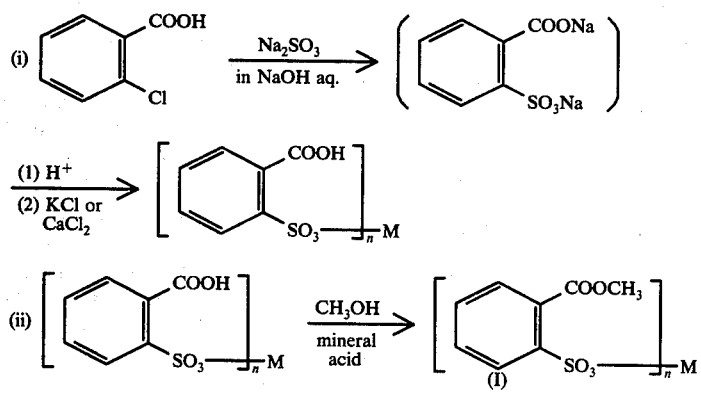

M and $n$ are defined in the equation above.

The process of the present invention involves a first step of producing methyl o-chlorosulfonylbenzoate as the intermediate by reacting phosgene with the methylbenzoate-o-sulfonate (I) in an inert organic solvent in the presence of dimethylformamide with stirring at relatively low temperature. In the next step, the reaction mixture produced in the first step is reacted with ammonia while stirred at relatively low temperature. The desired o-sulfobenzimide compound (II) is produced as an ammonium salt thereof in the second reaction step and can be easily separated in the acid form by precipitation with a mineral acid.

An inert organic solvent can be used in the first step of the reaction and suitable organic solvents include haloaliphatic hydrocarbons such as chloroform, carbon tetrachloride, dichloroethane, dichloropropane, and the like; and aromatic hydrocarbons such as benzene, tolua colored o-sulfobenzimide compound (II), and also resulting in a decreased yield of product. The reaction time is dependent upon the method of supplying phosgene, and is less than 7 hours, preferably 2–6 hours. After the reaction, nitrogen gas is passed into the reaction mixture to remove excess phosgene, and a metal chloride such as potassium chloride or calcium chloride and dimethylformamide are removed by washing the solution with water. The resulting methyl o-chlorosulfonylbenzoate can be used in the reaction of the second step in the form of the inert organic solvent solution without separation by distillation, or some other technique.

In the second reaction step of the present process it is possible to directly introduce ammonia gas into the reaction product produced in the first step after unreacted phosgene, the metal chloride by-product and dimethylformamide are removed. Ammonia can also be added to the first step reaction solution as an aqueous solution of ammonia. The amount of ammonia employed is usually in a range of 3-8 mole, preferably 3.5-4.5 mole per mole of the methylbenzoate-o-sulfonic acid group in compound (I). Normally, 4-28%, preferably 5-20% of an aqueous solution of ammonia is used in the reaction. The reaction of the second step is conducted at 0°-70° C, preferably 5°-40° C. After the reaction, the reaction mixture is separated into an organic phase and an aqueous solution phase. The desired o-sulfobenzimide compound (II) is present in the aqueous solution phase as the ammonium salt thereof. The desired o-sulfobenzimide compound (II) can be separated as crystals by adding a mineral acid such as hydrochloric acid or sulfuric acid to the aqueous solution phase after the phase separation to adjust the pH to 1-2.

By the process of the present invention, an o-sulfobenzimide (II) of high purity can be produced in yield greater than 85% based on the initial amount of methylbenzoate-o-sulfonate (I) with substantial industrial efficiency. The following are the characteristics and advantages of the process of the present invention.

1. By the process of the invention, methyl o-chlorosulfonylbenzoate can be easily produced by mild reaction conditions from a metal salt of methylbenzoate-o-sulfonic acid, and the product o-sulfobenzimide can be produced in high yield without any complicated separation or purification technique of methyl o-chlorosulfonylbenzoate.

2. The product o-sulfobenzimide can be produced in high purity without the simultaneous production of toluenesulfonamide which may be toxic. Accordingly, the o-sulfobenzimide produced by the process of the invention can be safely used as a food additive for human beings.

3. Phosgene which is economical and easily available can be used as the chlorinating agent. Accordingly, the process of the invention is industrially advantageous in comparison with other conventional processes which use expensive chlorinating agents such as phosphorus pentachloride, phosphorus oxychloride and the like.

The invention will be further illustrated by certain specific examples of the preparation of methylbenzoate-o-sulfonates (I) and certain other examples and references.

PREPARATION OF STARTING MATERIAL 1

Preparation of potassium methylbenzoate-o-sulfonate

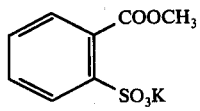

1. Into a 300 ml autoclave, was charged 150 ml of water. A 15.3 g (0.383 mole) amount of sodium hydroxide and 60 g (0.383 mole) of o-chlorobenzoic acid were dissolved in water, and then 53.1 g (0.421 mole) of sodium sulfite and 0.18 g (0.00114 mole) of cupric sulfate were charged to the autoclave with the o-chlorobenzoic solution. The mixture was stirred at 160°-170° C for 8 hours. During the reaction, the pressure in the autoclave was kept at 5-6 Kg/cm². After the reaction, the reaction mixture in the autoclave was cooled and removed. Conc. hydrochloric acid was added to the reaction mixture to adjust the pH to 2, and the small amount of unreacted o-chlorobenzoic acid was precipitated and filtered. A 55 g (0.74 mole) amount of potassium chloride was added to the filtrate, and the mixture was heated at 100° C to dissolve the potassium chloride. The solution was then cooled to room temperature, whereby 86.6 g of white crystals of the potassium salt of o-sulfobenzoic acid were precipitated.

2. Into a 300 ml autoclave, all of the white crystals of the potassium salt of sulfobenzoic acid produced in reaction (1) and 120 g (3.75 mole) of methanol and 2.68 (0.0268 mole) of 98% sulfuric acid were charged. The mixture was stirred at 100° C for 3 hours. The pressure of the autoclave was kept at 3.5 Kg/cm². After the reaction, the precipitated crystals were filtered whereby 87.0 g of white crystals of potassium methylbenzoate-o-sulfonate (yield of 84.9% based on o-chlorobenzoic acid) were obtained.

PREPARATION OF STARTING MATERIAL 2

Preparation of calcium methylbenzoate-o-sulfonate

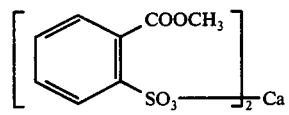

The same procedure for the Preparation of Starting Material 1 was used except that calcium chloride was used instead of potassium chloride. Reactions (1) and (2) were conducted whereby 78.4 g of white crystals of calcium methylbenzoate-o-sulfonate (yield of 83.5% based on o-chlorobenzoic acid) were obtained.

EXAMPLE 1

First Step

Into a 500 ml four-necked flask equipped with a stirrer, a thermometer, a condenser and a phosgene inlet, 87.0 g (0.325 mole) of potassium methylbenzoate-o-sulfonate, 300 ml of chlorobenzene and 1.36 g (0.0192 mole) of dimethylformamide were charged. A 37.0 g (0.374 mole) amount of phosgene was introduced into the mixture at 40° C for 3 hours with stirring. After the reaction, nitrogen gas was injected into the flask to remove unreacted phosgene. The reaction mixture was washed with 200 ml of water thereby a transparent pale yellow chlorobenzene solution of methyl o-chlorosulfonylbenzoate was obtained.

Second Step

Into a 1 liter four-necked flask equipped with a stirrer, a thermometer, a condenser and a dropping funnel, all of the chlorobenzene solution produced in the first step was charged and 220 g of 10% aqueous solution of ammonia (1.29 mole of ammonia) was added dropwise to the solution at 20° C with vigorous stirring. The reaction was continued for 4 hours. After the reaction, the organic phase was separated from the aqueous solution phase, and 6N-HCl was added dropwise to the aqueous solution phase with stirring to adjust the pH to 1.0. The resulting precipitated crystals were filtered, washed with 60 ml of cold water and dried whereby 53.5 g of white crystals of o-sulfobenzimide having a melting point of 227°-229° C (yield of 89.9% based on potassium methylbenzoate-o-sulfonate) were obtained. The purity of the resulting o-sulfobenzimide was 99.8% according to neutralization titration analysis.

REFERENCE EXAMPLE 1

The process of Example 1 was used except that no dimethylformamide was used in the first step. As a result, methyl o-chlorosulfonylbenzoate was not produced and only potassium methylbenzoate-o-sulfonate starting material was recovered.

EXAMPLE 2

In accordance with the process of Example 1, phosgene was introduced into an inert solvent solution of each metal methylbenzoate-o-sulfonate compound (I) shown in Table 1 in the presence of dimethylformamide and the first step of the reaction sequence was conducted. An aqueous solution of ammonia was then added to the reaction product in the second step and the product o-sulfobenzimide was precipitated with an acid. The starting materials, and the reaction conditions of the first and second steps are shown in Table 1 and the results are shown in Table 2.

Table 1

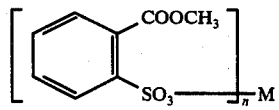
(I)

| Experiment | Starting Material | Amount (mol) |
|---|---|---|
| Example 1 | (o-COOCH₃, o-SO₃K benzene) | 0.325 |
| Example 2 (1) | [(o-COOCH₃, o-SO₃)benzene]₂-Ca | 0.160 |
| Example 2 (2) | (o-COOCH₃, o-SO₃K benzene) | 0.325 |
| Example 2 (3) | (o-COOCH₃, o-SO₃K benzene) | 0.325 |
| Example 2 (4) | (o-COOCH₃, o-SO₃K benzene) | 0.325 |
| Reference No. 1 | (o-COOCH₃, o-SO₃K benzene) | 0.325 |
| Reference No. 2 | (o-COOCH₃, o-SO₃K benzene) | 0.325 |

| | First Step | | | | | Second Step | | |
|---|---|---|---|---|---|---|---|---|
| | Amount of DMF (mol) | Solvent Amount (ml) | Amount of phosgene (mol) | Reaction Temp. (° C) | Cond. Time (hr) | Amount of 10% NH₃ aq. | Reaction Temp. (° C) | Cond. Time (hr) |
| Exp. 1 | 0.0163 | PhCl 300 | 0.374 | 40 | 5 | 1.29 | 20 | 4 |
| Exp. 2 (1) | 0.0160 | PhCl 300 | 0.368 | 40 | 5 | 1.28 | 20 | 4 |
| Exp. 2 (2) | 0.0163 | CCl₄ 300 | 0.374 | 40 | 5 | 1.29 | 20 | 4 |
| Exp. 2 (3) | 0.026 | PhCH₃ 300 | 0.374 | 40 | 5 | 1.29 | 20 | 4 |
| Exp. 2 (4) | 0.0016 | PhCl 300 | 0.374 | 40 | 12 | 1.29 | 20 | 4 |
| Ref. 1 No.1 | 0 | PhCl 300 | 0.374 | 40 | 5 | Starting material was recovered | | |
| Ref. 2 No. 2 | 0.065 | PhCl 300 | 0.374 | 40 | 5 | 1.29 | 20 | 4 |

Note:
DMF: dimethylformamide
PhCl: chlorobenzene
CCl₄: carbon tetrachloride
PhCH₃: toluene Table 2

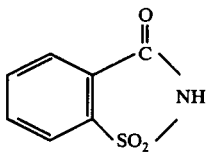
(II)

| Product | Amount of Product (g) | Yield (%) | Purity (%) |
| --- | --- | --- | --- |
| Exp. 1 | 53.5 | 89.9 | 99.8 |
| Exp. 2 (1) | 52.7 | 88.5 | 99.8 |
| Exp. 2 (2) | 51.4 | 86.3 | 99.8 |
| Exp. 2 (3) | 52.6 | 88.3 | 99.7 |
| Exp. 2 (4) | 49.5 | 83.1 | 99.8 |
| Ref. 1 No. 1 | | | |
| Ref. 2 No. 2 | 46.7 | 78.5 | 98.7 |

We claim:

1. A process for producing o-sulfobenzimide having the formula:

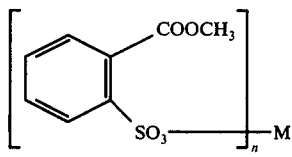

which comprises:
reacting phosgene with a methylbenzoate-o-sulfonate having the formula:

(I)

$$\left[ \begin{array}{c} \text{COOCH}_3 \\ \text{SO}_3^- \end{array} \right]_n \text{M}$$

wherein M represents potassium or calcium, $n$ is 1 when M is K and $n$ is 2 when M is Ca, in an inert organic solvent in the presence of dimethylformamide;
reacting ammonia with the reaction product to form the ammonium salt of said o-sulfobenzimide; and converting said ammonium salt to said o-sulfobenzimide.

2. The process according to claim 1, wherein phosgene gas is introduced into the inert organic solvent solution of the methylbenzoate-o-sulfonate compound (I) in the presence of dimethylformamide.

3. The process according to claim 1, wherein an inert organic solvent solution of phosgene is added to the inert organic solvent solution of the methylbenzoate-o-sulfonate compound (I) in the presence of dimethylformamide.

4. The process according to claim 1, wherein ammonia gas is introduced into the second step of the reaction to react with said reaction product.

5. The process according to claim 1, wherein an aqueous solution of ammonia is admixed with the reaction solution to react with said reaction product.

6. The process according to claim 1, wherein the methylbenzoate-o-sulfonate compound (I) is potassium methylbenzoate-o-sulfonate.

7. The process according to claim 1, wherein the methylbenzoate-o-sulfonate compound (I) is calcium methylbenzoate-o-sulfonate.

8. The process according to claim 1, wherein the amount of said dimethylformamide employed is in the range of 0.01 to 0.3 mole per mole of methylbenzoate-o-sulfonic acid groups in the methylbenzoate-o-sulfonate compound (I).

9. The process according to claim 1, wherein said inert organic solvent is a haloaliphatic hydrocarbon or an aromatic hydrocarbon.

10. The process according to claim 1, wherein the amount of ammonia is from 3-8 moles per mole of the methylbenzoate-o-sulfonic acid groups in compound I.

11. The process of claim 1, which further comprises:
after said ammonia reaction step, separating the aqueous phase of the reaction product from the organic phase; and
adjusting the pH of said aqueous phase to from 1 to 2 to generate said o-sulfobenzimide.

* * * * *